United States Patent [19]

Toyoshima et al.

[11] 4,328,216

[45] May 4, 1982

[54] NOVEL ORGANOSILICON COMPOUNDS AND ANTI-TUMOR AGENTS CONTAINING THE SAME

[75] Inventors: Shigeshi Toyoshima, Funabashi; Ryuichi Sato, Gunma; Koichi Ito, Higashi-Kurume; Toshio Shinohara, Annaka; Yasushi Yamamoto, Takasaki; Shoji Ichinohe, Annaka, all of Japan

[73] Assignee: Shin-Etsu Chemical Co., Ltd., Tokyo, Japan

[21] Appl. No.: 102,225

[22] Filed: Dec. 10, 1979

[30] Foreign Application Priority Data

Dec. 19, 1978 [JP] Japan ................ 53-160326

[51] Int. Cl.$^3$ ............. A61K 31/695; C07F 7/10
[52] U.S. Cl. ................ 424/184; 556/419
[58] Field of Search ............ 556/419; 424/184

[56] References Cited

U.S. PATENT DOCUMENTS 3,068,152 12/1962 Black ......................... 556/419

OTHER PUBLICATIONS

Noller, *Chemistry of Organic Compounds*, W. B. Saunders Co., Philadelphia, Pa., (1957), pp. 237 and 244.

*Primary Examiner*—Natalie Trousof
*Assistant Examiner*—Vera C. Clarke
*Attorney, Agent, or Firm*—Toren, McGeady & Stanger

[57] ABSTRACT

The invention provides a novel anti-tumor agent highly effective for inhibiting growth of several tumor or cancer cells with low toxicity. The active ingredient contained in the anti-tumor agent is an ω-triorganosilyl-substituted linear alkanoic acid anilide which is a hitherto unknown novel compound prepared by the reaction of corresponding acid chloride and aniline.

8 Claims, No Drawings

NOVEL ORGANOSILICON COMPOUNDS AND ANTI-TUMOR AGENTS CONTAINING THE SAME

BACKGROUND OF THE INVENTION

The present invention relates to a novel class of organosilicon compounds and an anti-tumor agent containing the organosilicon compound as the therapeutically effective ingredient. More particularly, the invention relates to ω-triorganosilyl-substituted linear alkanoic acid anilides and an anti-tumor agent containing a therapeutically effective amount of the same.

There have been hitherto known various kinds of organosilicon compounds having anti-tumor activity. For example, silatolan compounds belong to one of the classes of such organosilicon compounds having anti-tumor activity although silatolan compounds are not widely used in the actual therapy because of the relatively strong toxicity of the compounds. Other classes of organosilicon compounds also suffer from similar problems and, accordingly, there has been a strong desire to obtain a novel class of organosilicon compounds effective as an anti-tumor agent with low or no toxicity.

SUMMARY OF THE INVENTION

The primary object of the present invention is to provide a novel class of organosilicon compounds having activity as an anti-tumor agent and yet having low or no toxicity.

Another object of the invention is to provide a novel organosilicon compounds not described in any prior art literatures.

The novel organosilicon compound, which is the main ingredient contained in a therapeutically effective amount in the inventive anti-tumor agent, is represented by the general formula

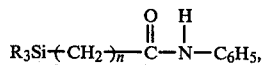
(I)

where R is a substituted or unsubstituted monovalent hydrocarbon group having from 1 to 10 carbon atoms and n is an integer from 1 to 5 inclusive.

The anti-tumor agent containing the compound of the above general formula (I) in a therapeutically effective amount exhibits strong anti-tumor activity with extremely low toxicity.

DETAILED DESCRIPTION OF THE PREFERRED EMBODIMENTS

The ω-triorganosilyl-substituted linear alkanoic acid anilide as the main ingredient of the inventive anti-tumor agent is represented by the above given general formula (I) and belongs to a class of novel organosilicon compounds hitherto not known or not described in any prior art literatures.

In the general formula (I), R is a substituted or unsubstituted monovalent hydrocarbon group having from 1 to 10 carbon atoms as exemplified by alkyl groups such as methyl, ethyl, propyl, butyl and the like, alkenyl groups such as vinyl, allyl and the like, cycloalkyl groups such as cyclohexyl and the like, aryl groups such as phenyl and the like and aralkyl groups such as phenylethyl and the like as well as those groups derived from the above named hydrocarbon groups by the substitution of, for example, halogen atoms for part or all of the hydrogen atoms in the hydrocarbon groups as exemplified by chloromethyl, 3,3,3-trifluoropropyl, 2-, 3- or 4-chlorophenyl, 3,4-dichlorophenyl and the like. Preferable groups represented by the symbol R are methyl, ethyl and phenyl groups. Three of the groups R in a molecule may be identical each with the others or may be different from each other.

The symbol n stands for an integer from 1 to 5 but, preferably, n is 1, 2 or 3.

Thus, several of the examples of the compounds in conformity with the general formula (I) and with the definitions of R and n are 3-trimethylsilylpropionic anilide, 4-trimethylsilylbutyric anilide, dimethylphenylsilyl acetanilide, 3-diethylmethylsilylpropionic anilide and the like.

The anilide compounds of the invention can be synthesized by the dehydrochlorination condensation of an ω-triorganosilyl-substituted linear alkanoic acid chloride represented by the general formula

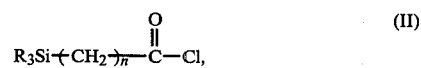
(II)

where R and n have the same meanings as defined above, with aniline, if necessary, in the presence of a tertiary amine, e.g. triethylamine, as an acceptor for hydrogen chloride. The tertiary amine can be omitted when the reaction mixture contains an excess amount of aniline which serves as an acid acceptor. The reaction is expressed by the following equation.

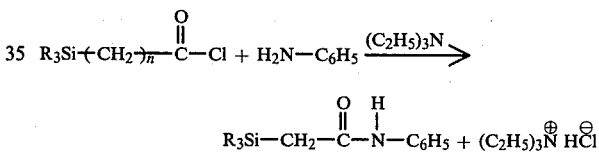

The above reaction can be performed by gradually adding the acid chloride into a solution of aniline in an organic solvent such as toluene followed, if necessary, by heating.

The reaction product thus obtained is, if necessary, washed with water and freed from volatile matters under reduced pressure to give the desired anilide compound of the general formula (I). The anilide compounds of the invention are in general soluble to some extent in aliphatic or alicyclic hydrocarbon solvents and soluble very well in most of the other organic solvents but almost insoluble in water.

The acid chloride suitable as the starting reactant in the above reaction is exemplified by 3-trimethylsilylpropionyl chloride, 4-trimethylsilylbutyryl chloride, dimethylphenylsilylacetyl chloride, 3-diethylmethylsilylpropionyl chloride and the like.

Following are the examples to illustrate the preparation of some of the inventive anilide compounds and the effectiveness of the compounds as the main ingredient of an anti-tumor agent.

PREPARATION 1

Synthesis of 4-trimethylsiylbutyric anilide

Into a solution of 19.5 g (0.21 mole) of aniline dissolved in 100 ml of toluene was added dropwise 17.7 g (0.1 mole) of 4-trimethylsilylbutyryl chloride and, after completion of addition of the chloride, the reaction mixture was heated at 50° to 60° C. for 1 hour to effect the reaction followed by washing with water. The organic solution separated from the aqueous phase was concentrated under reduced pressure and the product was purified by chromatography with silica gel as the adsorbent to give 22.3 g of a purified product having a melting point of 54°–56° C. which was identified by the elementary analysis, of which the analytical results are given below, infrared absorption spectral analysis and nuclear magnetic resonance absorption spectral analysis to be the objective 4-trimethylsilylbutyric anilide. The above given yield was 95% of the theoretical value.

Results of elementary analysis

|   | Found, % | Calculated as $C_{13}H_{21}ONSi$, % |
|---|---|---|
| C | 66.5 | 66.3 |
| H | 8.9 | 9.0 |
| Si | 11.8 | 11.9 |
| N | 6.1 | 6.0 |

PREPARATION 2

Synthesis of dimethylphenylsilyl acetanilide

Into a solution of 9.8 g (0.11 mole) of aniline and 15 g (0.15 mole) of triethylamine dissolved in 100 ml of toluene was added dropwise 21.3 g (0.1 mole) of dimethylphenylsilylacetyl chloride and, after completion of the addition of the chloride, the reaction mixture was heated at 50°–60° C. for 1 hour to effect the reaction followed by removal of the volatile matter. The reaction product thus obtained was purified by recrystallization from n-hexane to give 24.2 g of a purified product having a melting point of 88°–89° C. which was identified to be the objective dimethylphenylsilyl acetanilide. The above given yield was 90% of the theoretical value.

Results of elementary analysis

|   | Found, % | Calculated as $C_{16}H_{19}ONSi$, % |
|---|---|---|
| C | 71.2 | 71.3 |
| H | 7.0 | 7.1 |
| Si | 10.3 | 10.4 |
| N | 5.4 | 5.2 |

PREPARATION 3

Synthesis of 4-diethylmethylsilylbutyric anilide

The synthetic procedure was about the same as in the above Preparation 2 and 23.7 g of a reaction product having a melting point of 147°–149° C., which was identified to be 4-diethylmethylsilylbutyric anilide, was obtained with 15.2 g (0.15 mole) of triethylamine, 9.8 g (0.11 mole) of aniline and 20.7 g (0.1 mole) of 4-diethylmethylsilylbutyryl chloride. The above given yield was 93% of the theoretical value.

Results of elementary analysis

|   | Found, % | Calculated as $C_{14}H_{23}ONSi$, % |
|---|---|---|
| C | 68.5 | 68.4 |
| H | 9.7 | 9.6 |
| Si | 10.4 | 10.7 |
| N | 6.2 | 6.3 |

Test 1

Each of the female mice belonging to the test group and the control group, each group being composed of six $BDF_1$ female mice, was inoculated with $5.7 \times 10^5$ cells of B-16 melanoma subcutaneously. The mice belonging to the control group were bred continuously as such while each of the mice belonging to the test group was administrated with 300 mg every day of 4-trimethylsilylbutyric anilide prepared in Preparation 1 above and dispersed in olive oil by intraperitoneal injection beginning on the next day and ending on the sixth day of the inoculation. After 14 days from the transplantation of the tumor cells, the mice were killed and the average weight of the tumor was determined to give the results that the value was $1.1186 \pm 0.9283$ g for the control group and $0.5973 \pm 0.5435$ g for the test group.

The inhibiting efficiency calculated with the above results by the following equation was 46.6%.

Inhibiting efficiency =

$$\frac{\left(\begin{array}{c}\text{Average weight}\\\text{of tumor in the}\\\text{control group}\end{array}\right) - \left(\begin{array}{c}\text{Average weight}\\\text{of tumor in the}\\\text{test group}\end{array}\right)}{\left(\begin{array}{c}\text{Average weight of tumor in the}\\\text{control group}\end{array}\right)}$$

Test 2

The test was carried out in the same manner as in Test 1 above except that 4-trimethylsilylbutyric anilide was replaced with dimethylphenylsilyl acetanilide prepared in Preparation 2 above. The inhibiting efficiency calculated from the average tumor weights in the control group and the test group was 46.3%.

Test 3

The test was carried out in the same manner as in Test 1 above except that 4-trimethylsilylbutyric anilide was replaced with 4-diethylmethylsilylbutyric anilide prepared in Preparation 3 above. The inhibiting efficiency calculated from the average tumor weights in the control group and the test group was 45.1%.

Comparative Test 1

The test was carried out in the same manner as in Test 1 above except that 4-trimethylsilybutyric anilide was replaced with 5-fluorouracil. The inhibiting efficiency calculated from the average tumor weights in the control group and the test group was 21.6%.

Test 4

Each of the female mice belonging to the test group and the control group, each group being composed of six female $BDF_1$ mice, was inoculated with $5 \times 10^5$ cells of Lewis lung cancer subcutaneously. The mice belonging to the control group were bred continuously as such while each of the mice belonging to the test group was administrated with 300 mg every day of 4-trimethylsilylbutyric anilide as dispersed in olive oil by intraperitoneal injection beginning on the next day and ending on the sixth day of the inoculation. After 14 days from the inoculation of the lung cancer cells, the average weight of the cancer cells was determined for the control group and the test group to find that the inhibiting efficiency was 93.4%.

Test 5

The test was carried out in the same manner as in test 4 above except that 4-trimethylsilybutyric anilide was replaced with dimethylphenylsilyl acetanilide. The inhibiting efficiency calculated from the average weights of the cancer cells in the control group and the test group was 92.1%.

Test 6

The test was carried out in the same manner as in test 4 above except that 4-trimethylsilylbutyric anilide was replaced with 4-diethylmethylsilylbutyric anilide. The inhibiting efficiency calculated from the average weights of the cancer cells in the control group and the test group was 90.5%.

Comparative Test 2

The test was carried out in the same manner as in Test 4 above except that 4-trimethylsilylbutyric anilide was replaced with 5-fluorouracil. The inhibiting efficiency calculated from the average weights of the cancer cells in the control group and the test group was 43.3%.

What is claimed is:

1. An ω-triorganosilyl-substituted linear alkanoic acid anilide represented by the formula

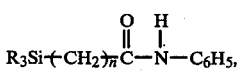

where R is a monovalent hydrocarbon group having from 1 to 10 carbon atoms, unsubstituted or substituted with halogen atoms and n is an integer from 1 to 5.

2. 4-Trimethylsilylbutyric anilide.
3. Dimethylphenylsilyl acetanilide.
4. 4-Diethylmethylsilylbutyric anilide.
5. An agent for inhibiting of melanoma and Lewis lung cancer comprising an ω-triorganosilyl-substituted linear alkanoic acid anilide represented by the formula

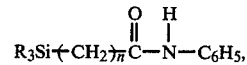

where R is a monovalent hydrocarbon group having from 1 to 10 carbon atoms unsubstituted or substit and n is an integer from 1 to 5, in a therapeutically effective amount and a carrier therefor.

6. The agent as claimed in claim 5 wherein the ω-triorganosilyl-substituted linear alkanoic acid anilide is 4-trimethylsilylbutyric anilide.

7. The agent as claimed in claim 5 wherein the ω-triorganosilyl-substituted linear alkanoic acid anilide is dimethylphenylsilyl acetanilide.

8. The agent as claimed in claim 5 wherein the ω-triorganosilyl-substituted linear alkanoic acid anilide is 4-diethylmethylsilylbutyric anilide.

* * * * *